(12) United States Patent
Potter et al.

(10) Patent No.: US 6,339,952 B1
(45) Date of Patent: Jan. 22, 2002

(54) HOT FILL APPARATUS AND PROCESS THEREFOR

(75) Inventors: Terry C. Potter, Lambertville, MI (US); Andrew E. Potter; Peter J. Hatas, both of Sylvania, OH (US)

(73) Assignee: Teadt, Rising, Burton & Associates, L.L.C., Maumee, OH (US)

( * ) Notice: Subject to any disclaimer, the term of this patent is extended or adjusted under 35 U.S.C. 154(b) by 0 days.

(21) Appl. No.: 09/632,078

(22) Filed: Aug. 4, 2000

Related U.S. Application Data

(60) Provisional application No. 60/147,995, filed on Aug. 10, 1999.

(51) Int. Cl.[7] .......................... G01M 3/04; G01M 3/02; A21D 10/00
(52) U.S. Cl. .................. 73/40; 73/37; 426/549
(58) Field of Search .................. 73/866, 37, 37.5, 73/37.6, 40, 41, 41.4, 45.1, 49.2; 215/398; 252/589; 264/101, 454; 426/271, 298, 489, 492, 549

(56) References Cited

U.S. PATENT DOCUMENTS

| 4,761,295 | A | * | 8/1988 | Casey .................. 426/549 |
| 5,011,648 | A | | 4/1991 | Garyer et al. |
| 5,746,808 | A | | 5/1998 | Hellenschmidt |

* cited by examiner

Primary Examiner—Hezron Williams
Assistant Examiner—Jay L. Politzer
(74) Attorney, Agent, or Firm—Emch, Schaffer, Schaub & Porcello Co., L.P.A.

(57) ABSTRACT

A hot fill apparatus for use in the testing of hollow thermoplastic containers, the apparatus having a reverse osmosis filter system, a heater system and a fill head system. The reverse osmosis filter system removes chlorine and other particulates and contaminants from the water prior to the water entering the heater system. The heater system is designed to maintain strict temperature control of the water while maintaining a steady flow rate and pressure. The fill head system includes a manually operated spigot and an automatically operated fill head, the operations of which are mutually exclusive.

15 Claims, 7 Drawing Sheets

HOT FILL APPARATUS AND PROCESS THEREFOR

This application claims the benefit of U.S. Provisional Appication(s) No.: 60/147,995 filed on Aug. 10, 1999.

BACKGROUND OF THE INVENTION

The present invention relates to a hot fill apparatus and process for use in the manufacture of hollow blow molded containers constructed from a thermoplastic, such as a thermoplastic polyester or a biaxially oriented polyethylene terephthalate resin. Hollow blow molded thermoplastics are commonly used as containers for food and beverages. Such containers, particularly containers constructed of a biaxially oriented polyethylene terephthalate resin ("PET"), must be periodically tested during manufacture for structural resiliency under hot fill and cold fill applications. For instance, in manufacturing operations producing between 5,000 and 50,000 containers per hour, batches of the containers are regularly tested, in many cases on an hourly basis, to ensure continued quality of manufacture. These requirements are met by a hot fill apparatus which fills the container with hot water, commonly maintained at a temperature close to boiling and then quick cools the container. The hot fill and quick cool application of water to a container provides a quality check of the resiliency of the container shape against expansion, contraction and undesirable deformation.

Flow through hot fill machines are designed to maintain a specified pressure and flow rate of water through the apparatus regardless of whether the apparatus is in use. Maintenance of flow rate and pressure are necessary to maintain strict regulation of water temperature within the hot fill apparatus. Some prior art hot fill machines will use at least one "instant heat" water heater and commonly use up to three such water heaters linked in combination to maintain strict temperature control of the water. Such water heaters demand a constant flow rate and a constant pressure of water passing through the heaters to prevent damage to the heaters. Commonly, the pressure is maintained at or above a required minimum of 20 psi and the flow rates are maintained at or above a required minimum of 1.5 gallons per minute with an optimum flow rate being 3 gallons per minute. Thus, some prior art flow-through hot fill machines have a water flow control system which provides a desired input volume into the heating loop and maintains a desired output volume from the heating loop. When the machine is not in use, the water output from the heating loop commonly enters a bypass flow to a drain.

Hot fill machines commonly have a number of faults which make them unreliable and many times undesirable.

Hot fill machines commonly work with conditioned water, water obtained from municipal water sources, and well water. Most water, even softened water, contains undesirable amounts of chemicals, minerals and other contaminants such that scale and chemical or mineral deposits will be formed, over time, on the heaters. An accumulation of scale or deposits on the heaters cause the heater mechanisms to become inefficient, resulting in premature failure and overloading of the heaters, thereby shutting down the machine and forcing costly repairs. Thus, it is desirable to provide a hot fill machine and process that can treat the input water prior to heating to remove undesirable chemicals, minerals and other contaminants.

Many common prior art hot fill machines use a spring activated valve or nozzle which is pressed upon the thermoplastic container mouth to open the valve and cause the hot fill water to flow into the container. Such spring activated valves sometimes put too much pressure on the container and have been known to deform or crush the container. A hot fill machine having a redesigned valve member is desired.

SUMMARY OF THE INVENTION

The present invention provides solutions to the above problems in the following manner. Water intended to flow to the heaters is first received from the water source and treated by a reverse osmosis filtration system. The reverse osmosis filtration system serves to trap and eliminate most all minerals and chemicals which are known to deposit upon and contaminate the heaters, thereby eliminating many known causes of heater inefficiency and premature failure. The reverse osmosis system as incorporated in this hot fill machine ideally uses a carbon canister having 2 parts per million chlorine removal capability with a backflush provision. The flow rate into the reverse osmosis system is designed to provide the desirable input flow into the heaters, thereby creating the desirable output flow from the heaters. The reverse osmosis system by nature of its operation creates an output flow rate which is less than the input flow rate, commonly by a ratio of three to one. For instance, one embodiment of the invention will input water at 6 gallons per minute into the reverse osmosis system to receive an output of clean uncontaminated water at 2 gallons per minute which flows to the heater mechanisms. The 4 gallons per minute flow differential is either recirculated back to the inlet side of the water pump or, if the water is heavily contaminated, is dumped to the drain. The reverse osmosis system, as incorporated into this invention, is designed with an automatic backwash for the carbon tanks which is operational when it is sensed within the hot fill apparatus that the system is in idle and not being used for hot fill applications.

The fill mechanism of the hot fill apparatus of this invention is normally provided with, for alternative usage, an on/off spigot and an automatic fill head. The spigot is used for any purpose and is not controlled by the height, volume and top load force variables which are used to control the fill head. The automatic fill head includes a rodless air cylinder with an adjustable slide through which an operator can dial in the bottle height and top load which is desired to simulate the load that a container will experience when filled with end product. Commonly, the top load is greater than 3 pounds, but less than 14 pounds. After the operator has established the bottle size and top load, the fill head is automatically activated to hot fill the container. Sensors act to sense the fill level and discontinue the fill and return the fill head to its original start position. Alternatively, controls are provided through which an operator can adjust the amount of fluid flowing into a container, thereby causing the fill head to automatically shut off. An override switch is also provided which can deactivate or activate the fill nozzle solenoid at any point in the cycle.

The hot fill machine is designed to have continuous flow and is provided with a normally open solenoid valve that directs flow to the drain and automatically closes when either the spigot or the fill head is activated. The spigot and fill head cannot be activated at the same time, thereby assisting and maintaining the controlled flow and temperature required for the proper operation of the hot fill apparatus.

These inventive aspects of the hot fill apparatus and process are achieved by the apparatus described and disclosed in the following drawings.

DESCRIPTION OF THE PREFERRED EMBODIMENT

Figure 1:
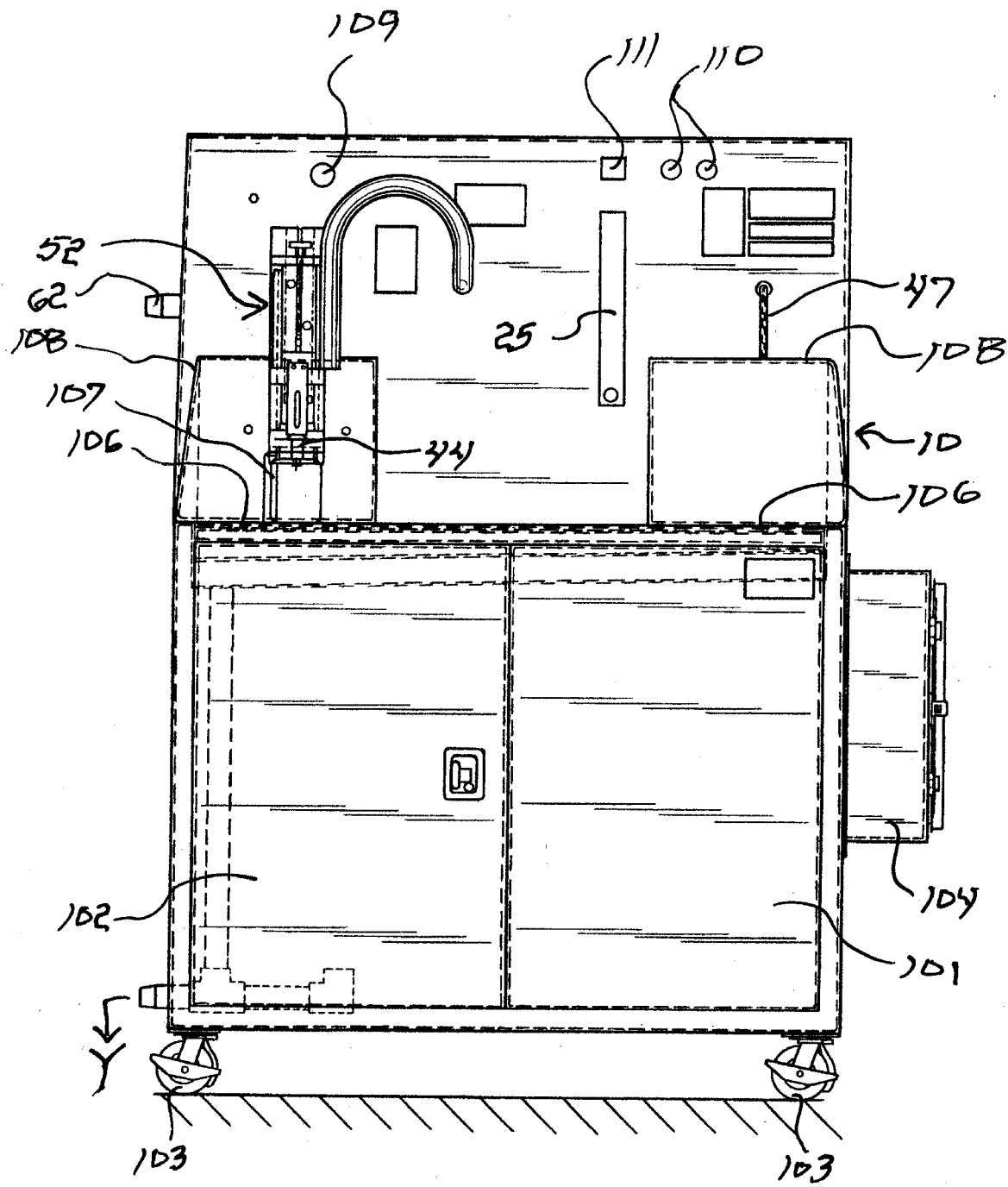
FIG. 1 is a front elevation view of the hot fill apparatus of the present invention.
Figure 2:
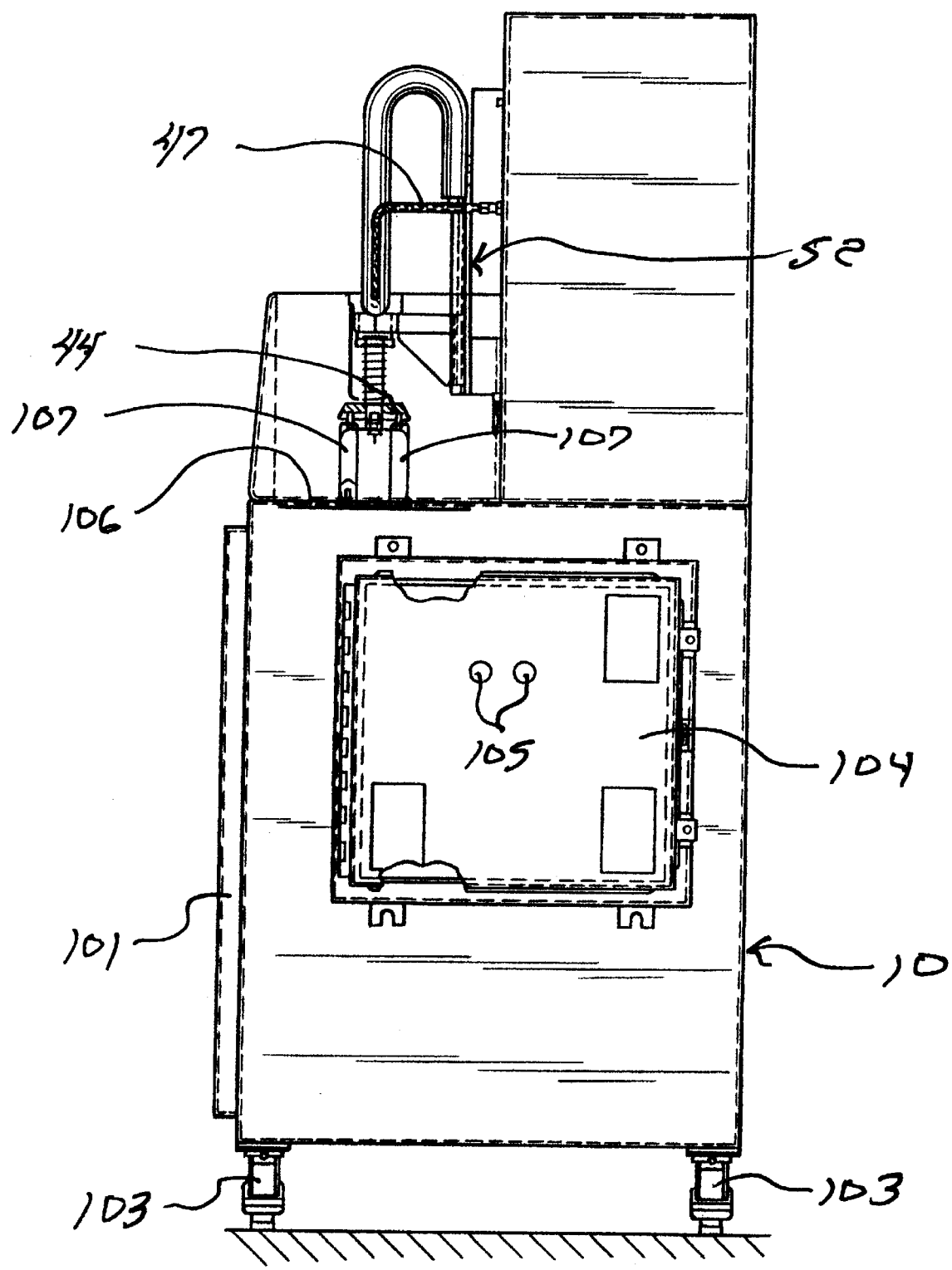
FIG. 2 is a right side elevation view of the hot fill apparatus of the present invention.
Figure 3:
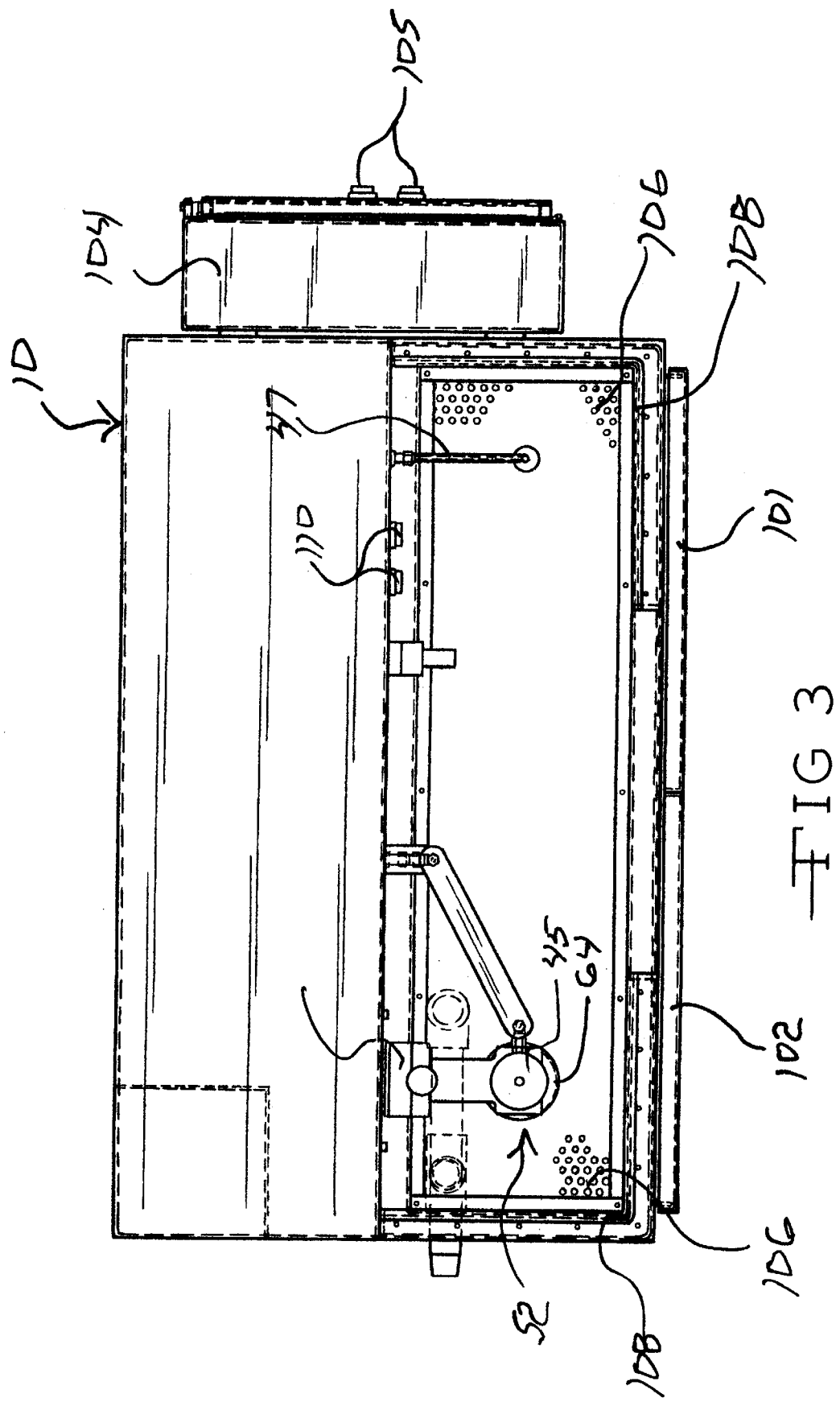
FIG. 3 is a top view of the hot fill apparatus of the present invention.

Referring now to FIGS. 1–3, the general structure of the hot fill apparatus of the present invention is shown. The preferred embodiment includes a cabinet casing 10 which houses a reverse osmosis filter system, heating system and the variety of control valves, gauges and inert tubing. While the description of the preferred embodiment of the invention describes a single unit housing the reverse osmosis system and heaters, it is easily envisioned that the reverse osmosis system can be physically separated from the heater and nozzle apparatus, thereby reducing the size of the hot fill machine and possibly allowing for more than one hot fill machine to be operated with a single reverse osmosis system.

FIG. 1 is a front view of the hot fill apparatus, wherein the cabinet 10 includes a pair of doors 101, 102, which when opened, provide access to the interior of the hot fill apparatus. The cabinet 10 rests upon a plurality of rollers 103 which allow the cabinet to be rolled around the work space and locked into position at a given location. A programmable logic controller or computer (PLC) 104 is mounted on the side of the cabinet 10. The PLC 104 controls the operation of the hot fill apparatus, including all systems contained therein. The exterior casing of the PLC is provided with an on/off switch 105 which activates and deactivates the entire hot fill apparatus.

The cabinet 10 includes a shelf and drain structure 106 which provides support for any thermoplastic bottles or containers which are placed under the spigot 47 or fill head 44. Structural locator members 107 are provided to retain a bottle or container in position with regard to the automated fill head 44. The area surrounding the spigot 47 and the area surrounding the automated fill head 44 are each enclosed by splash guards 108. A manual on/off PLC override switch 109 is provided for the automatic fill head 44 and on/off switches 110 are also provided for the activation and deactivation of the spigot 47. A flow meter 25 visible on the front of cabinet 10 of the hot fill apparatus provides a continuous readout of the water exiting the water entering the reverse osmosis system.

The fluid and water circuits of the preferred embodiment of the present invention will be described specifically with reference to FIGS. 6A and 6B. The various elements which comprise the reverse osmosis system, heating system and air pressure system are arranged within the cabinet casing 10.

Figure 6A:
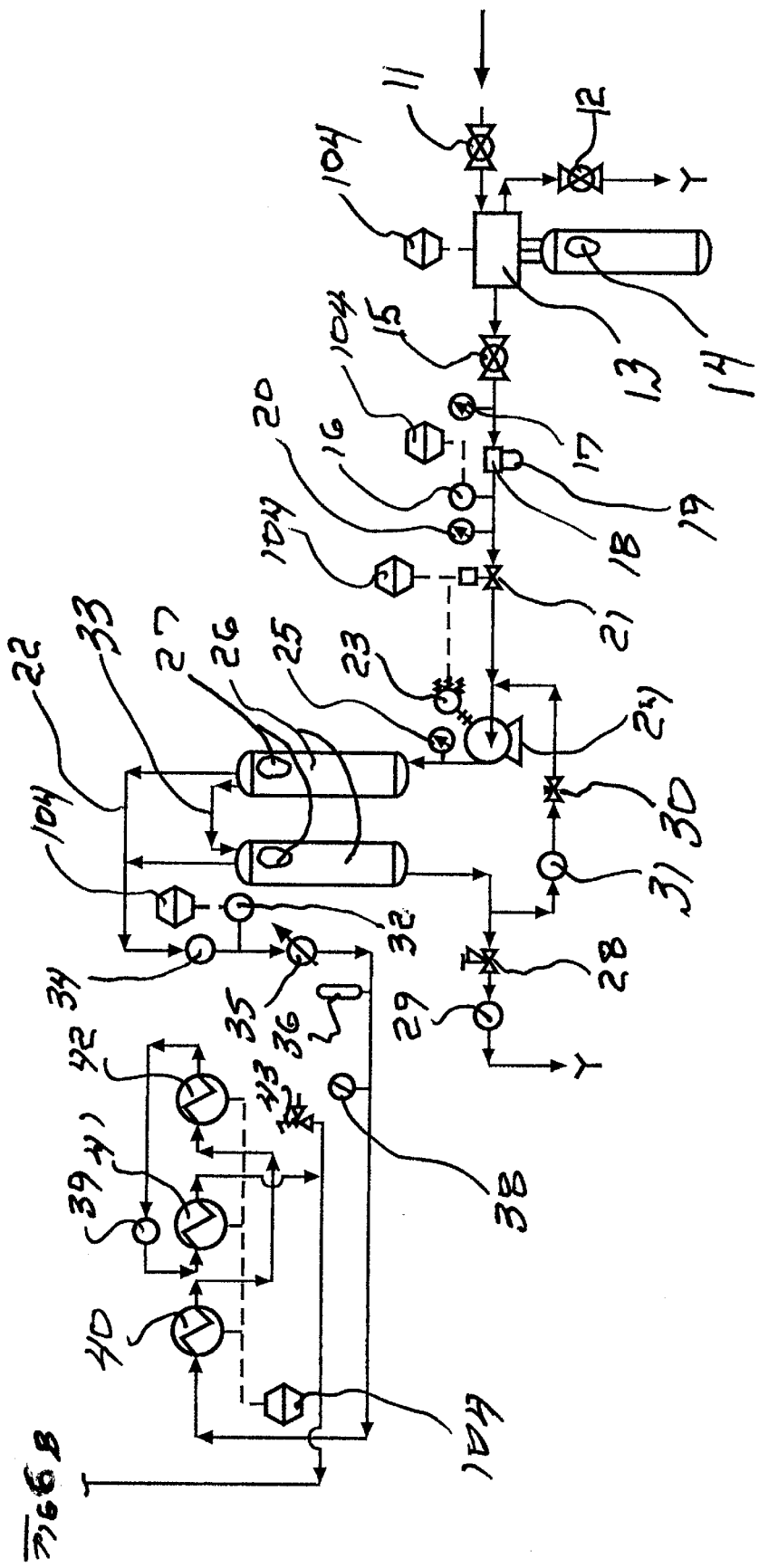
FIGS. 6A and 6B are a piping and pneumatic flow diagram for the hot fill apparatus of the present invention.
Figure 6B:
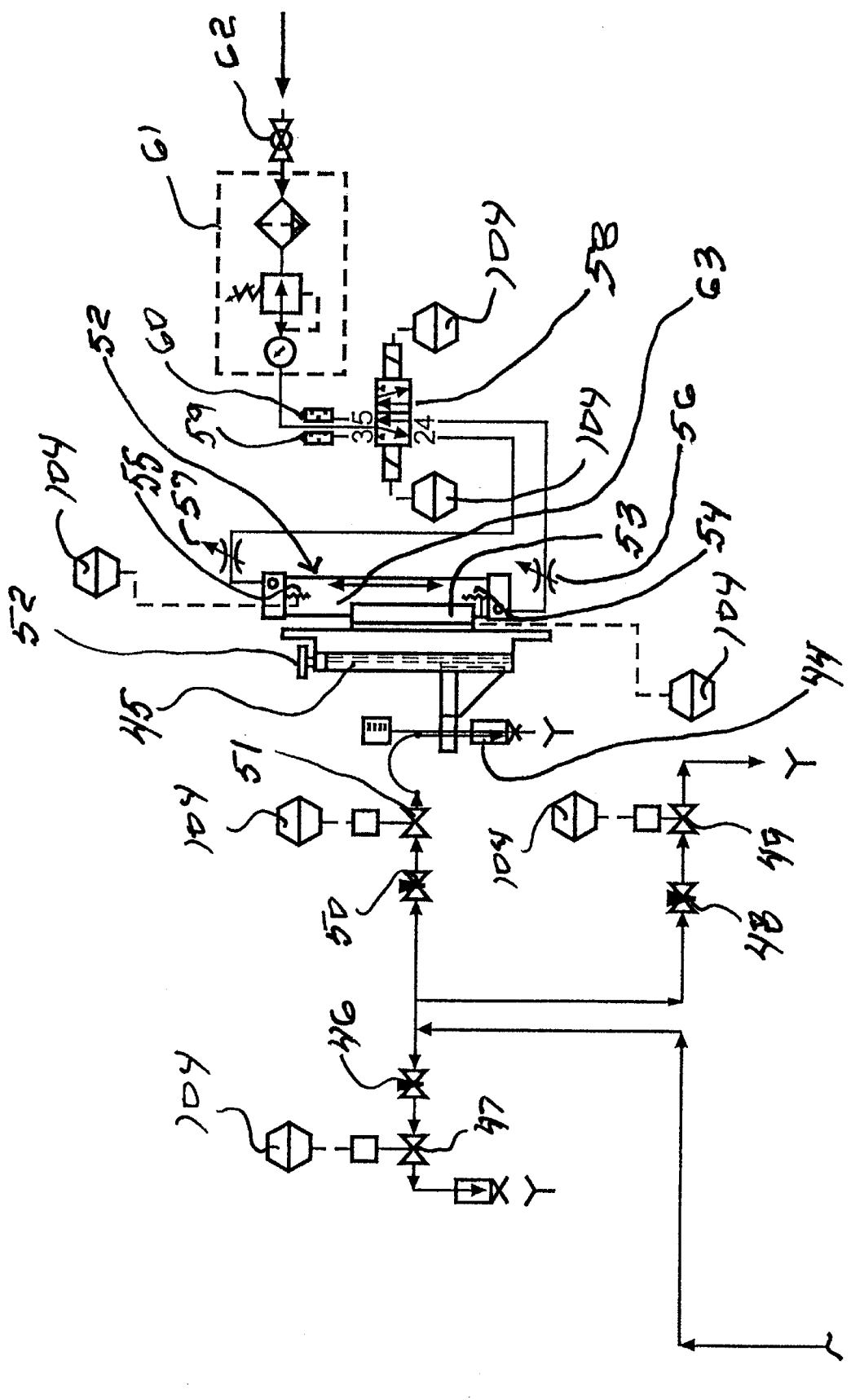

Referring to FIGS. 6A and 6B, water received from an outside source (not shown) enters the apparatus through ball valve 11 which introduces the water into the reverse osmosis system which includes a charcoal filter 14 for chlorine removal, a large particle filter 18 for large particulate removal and, preferably, two reverse osmosis filters 26. The ball valve 11 is designed to close when the interior water pressure within the hot fill apparatus is greater than the water pressure of the water flow from the outside source. The charcoal filter 14, for chlorine removal, includes a timer 13 which is engaged with the charcoal filter 14 to provide for timed backflushing of the charcoal filter 14 through backflush ball valve 12 to provide regular cleansing of the membrane materials within the charcoal filter 14. Timer 13 is linked to the programmable logic controller (PLC) 104 which controls the entire hot fill apparatus. As the chlorine-free water exits the chlorine filter 14, a flow switch 16, also receiving controlling input from the PLC 104, controls the flow of water from the charcoal filter 14 through incoming ball valve 15 and inlet pressure gauge 17. The incoming chlorine-free water then passes through a large particle filter 18 containing a filter element 19 intended to remove particles having a size of 10 microns or greater. An outlet pressure gauge 20 is provided to sense the differential between the inlet pressure to the filter 18 and the outlet pressure, thereby determining the need for filter replacement. If the outlet pressure gauge senses a high differential, it signals the PLC and the operator is notified to replace the filter element 19. The filtered chlorine-free water then passes through a solenoid operated valve 21 which is the automatic water feed for the reverse osmosis canisters 26. The solenoid operated valve 21 is controlled by the PLC 104 to provide a steady flow of water into the reverse osmosis system. A pump 24 operated by motor 23 is used to increase the pressure of the inlet water and the pressure of the inlet water is monitored by high pressure gauge 25, all of which are responsive to the PLC 104. The reverse osmosis canisters 26 will output water into the heaters at desired flow and pressure rates and the PLC 104 controls the flow and pressure rates of the input water into the reverse osmosis canisters 26 such that the water output to the heater system is maintained at a predetermined steady pressure and flow rate. For instance, the pump 24 is activated by the PLC 104 in one embodiment to input water at 6 gallons per minute into the reverse osmosis canisters 26, thereby receiving an output of clean uncontaminated water at 2 gallons per minute which flows to the heater system. The 4 gallons per minute differential of water flow is either recirculated back to the inlet side of the water pump 24 or, if the water is heavily contaminated, is dumped to the drain.

Each reverse osmosis canister 26 contains a reverse osmosis membrane filter 27. The reverse osmosis filters 27 will remove and eliminate most all minerals and chemicals within the water supply. As the water is filtered through the first filter 27A, cleansed water will exit the first filter 27A through clean water conduit 22. Water which is still contaminated will exit the first filter 27A and enter the second filter 27B through concentrate conduit 33. After passing through the second reverse osmosis filter 27B, clean water will again exit through clean water conduit 22 for transportation to the heater system and concentrate containing contaminated water will exit the second reverse osmosis filter 27B for either recycling back to the feed water lines leading to the reverse osmosis pump 24, or to be dumped to the drain. The contaminated concentrate will flow to the concentrate control regulator 28 which is preset by the PLC 104 to regulate the back pressure to the reverse osmosis filters 27A, 27B, and thereby control the pressure output from the reverse osmosis filters 27A, 27B to the heater system. A metering valve 30, also controlled by the PLC 104, works in combination with the concentrate control regulator 28 to determine whether the contaminated concentrate exiting the reverse osmosis filter 27B should be recycled for reuse or dumped to the drain. Flow meter 29 monitors the concentrate flow to the drain and flow meter 31 monitors the recycle flow.

As the clean water exits the reverse osmosis filters 27A, 27B through the clean water conduit 22, the clean water flows through the pressure switch 32 which controls the infeed pressure for the heater system and presets the water pressure to a predetermined level, preferably 20 psi. The clean infeed water, now flowing at the predetermined pressure, enters the flow meters 34, 35 which control the flow rate of the clean water and are manually adjustable to provide a desired flow rate of clean water into the heater system, preferably 2 gallons per minute. As the clean water flows to the heater system, it passes through a water hammer arrester 36 which protects the heater system from any surges in water pressure or flow rate. The clean water then passes through a final pressure gauge 38 which monitors the pressure feeding to the water heater system.

The heater system of the preferred embodiment is composed of a slave heater 40, a secondary slave heater 42 and a master heater 41. The slave heater includes a safety shutoff flow switch 39 which, if it detects a flow rate of less than ½ gallon per minute, will turn off the heater to prevent heater damage. The three heaters 40, 41 and 42 are ideally fed a constant flow of water at a constant pressure and operate to maintain the desired temperature of the water which is preferably slightly lower than boiling. The heaters are controlled by the PLC 104. The heated water exits the heater system and, referring now to FIG. 6B, either flows to the drain or flows to the hot fill valves. A pressure relief valve 43 will provide a safety bypass, if the pressure within the water heaters for some reason rises unexpectedly, allowing the release of pressure in the water lines and heater.

As the heated water exits the heater system, it has three options for flow. If the hot fill apparatus is not in use, the heated water flows through metering valve 48 and bypass valve 49, which is controlled by the PLC 104 to the drain. If the hot fill apparatus is in use, the water will flow to either a manually operated spigot 47 through metering valve 46 or it will flow through the automatic fill nozzle apparatus through metering valve 50.

Figure 4:
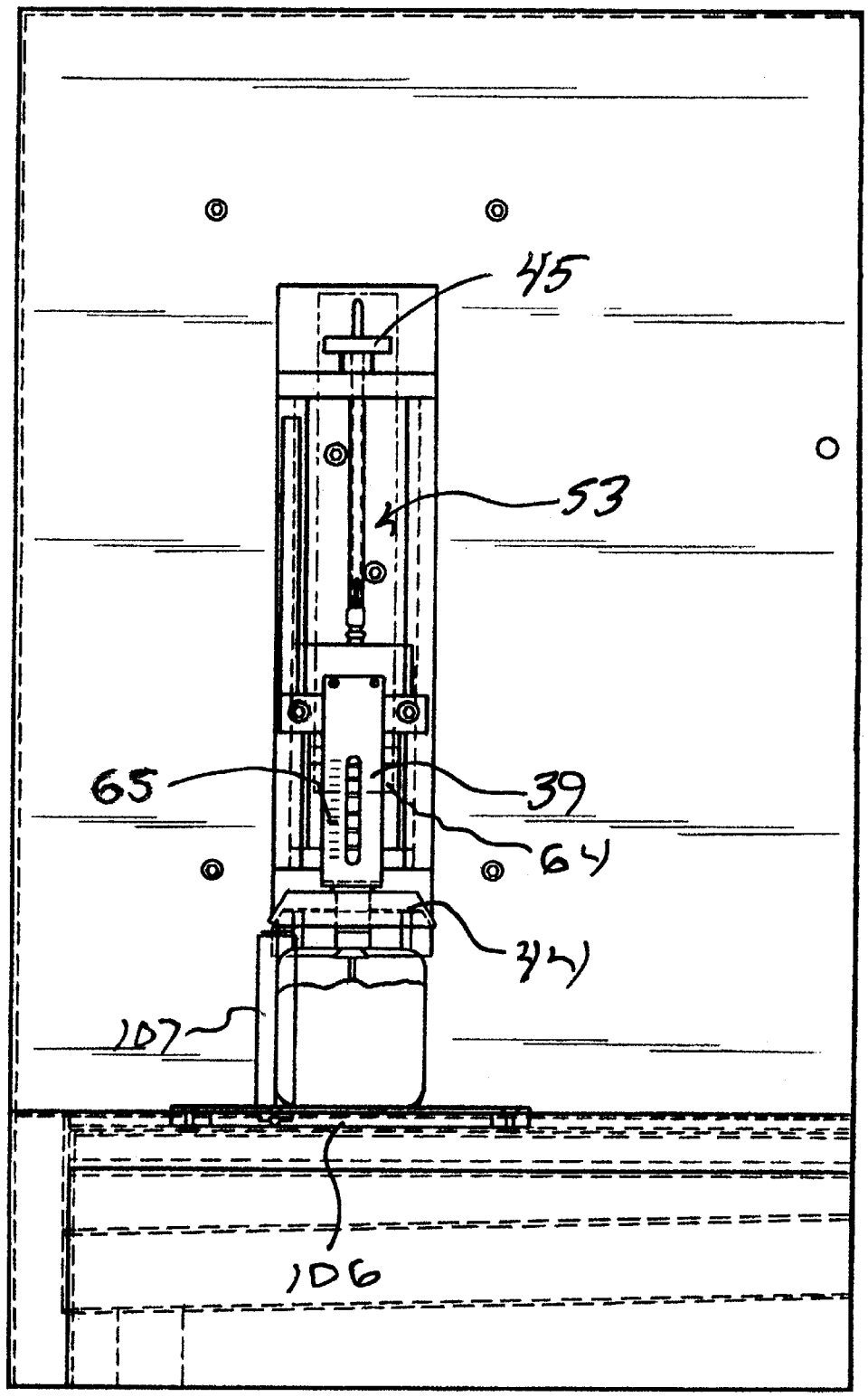
FIG. 4 is a front detail view of the automatic fill nozzle of the hot fill apparatus of the present invention.
Figure 5:
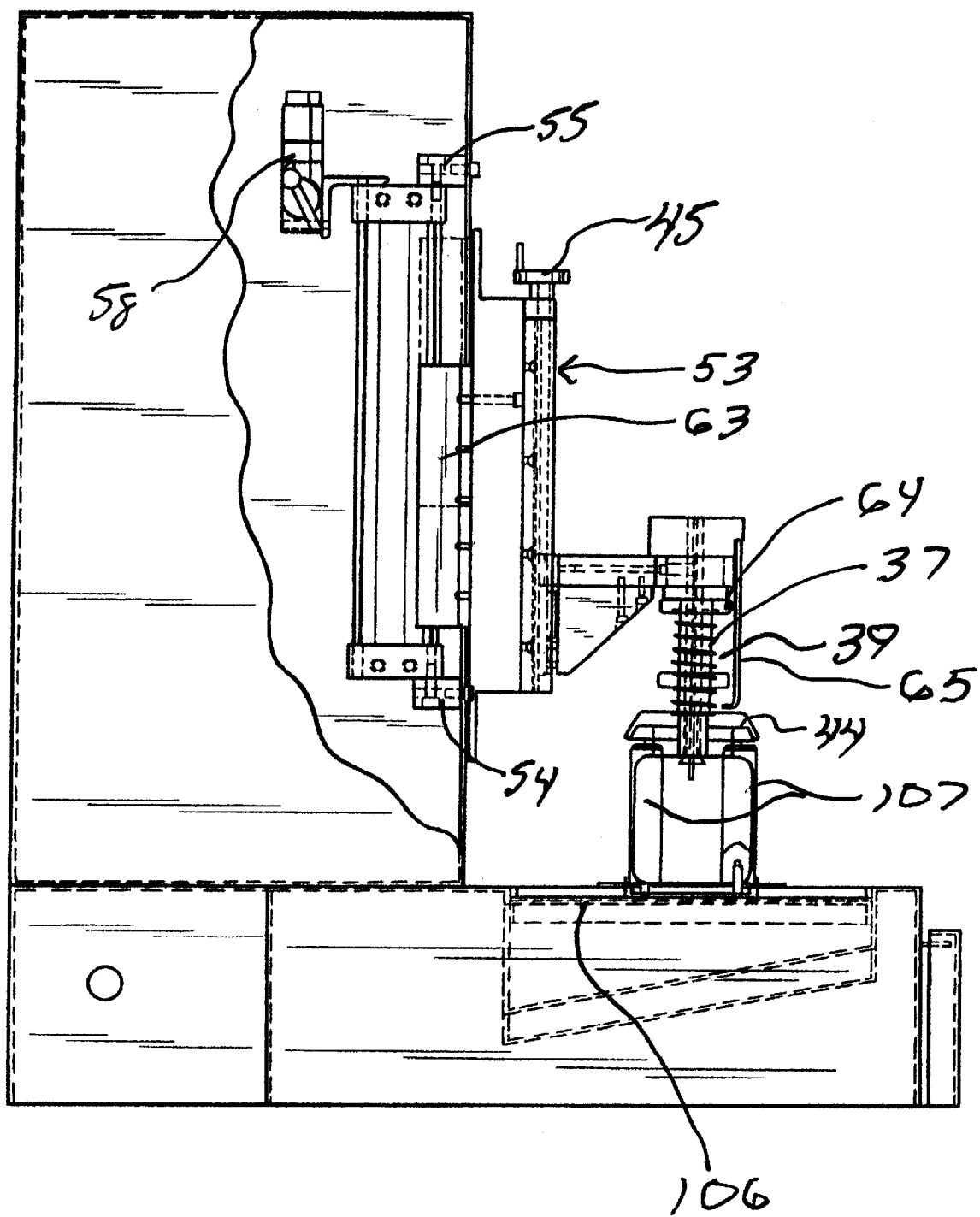
FIG. 5 is a side detail view of the automatic fill nozzle of the hot fill apparatus of the present invention.

Referring now to FIGS. 4, 5 and 6B, the fill nozzle apparatus consists of a fill nozzle valve 51 which is controlled by the PLC 104 and feeds water to the fill nozzle apparatus 52. The fill nozzle apparatus 52 consists of a carriage 53 positioned for vertical movement by an air cylinder 63 having a bottom position sensor 54 and a top position sensor 55. The carriage 53 carries a fill head 44 mounted on a manually adjustable fill head height controller 45 and a resilient adjustable top load member 39. The manually operated fill head height controller 45 is preferably used to make gross adjustments in the height of the fill head 44 while the force with which the automatic fill head engages the mouth of a container is controlled by top load member 39 and vertical movement of the fill head 44 which is activated by the automatic air pressure control system.

The top load member 39 includes a spring member 37 engaged between the fill head 44 and a manually adjustable dial 64. A scale 65 indicating top load force is positioned to allow the operator to "dial in" the desired top load force by operating the dial 64 to compress or decompress the spring member 37. The top load force is the desired force with which the fill head 44 engages the mouth of the container to test the ability of the container to withstand crushing or deforming forces during hot fill apparatus.

Referring to FIG. 6B, the automatic air pressure control system consists of an air inlet 62 which receives plant air which is processed through an inlet air filter and regulator 61 which sets the air pressure at, preferably, 40 psi. Exhaust silencers 59 and 60 are in place on the air line to quiet any air being exhausted from the air valve system when the hot fill apparatus is not in use. A solenoid control valve 58 is in communication with PLC 104 and is controlled thereby to feed air to the carriage cylinder 63 or exhaust air therefrom. When the air control system is engaged, the air pressure varies between speed control valves 56, 57, thereby controlling vertical movement of the carriage 53 to engage or disengage the fill head 44 with the container. The PLC 104 will determine, through input by the operator, the bottle size and will automatically move the fill head 44 by means of the carriage 53 from an unengaged position to an engaged position with the container to provide an appropriate seal thereto. Once the fill head is engaged with the container, the fill nozzle valve 51 opens to allow a predetermined amount of hot water as determined by the PLC 104 to fill the bottle. The programmable logic controller instructs the fill nozzle valve 51 when to discontinue the flow of water through the fill nozzle and return the flow of water to dump to the drain.

The above description of the preferred embodiment of the hot fill apparatus of this invention is intended to be illustrative in nature and not limiting upon the scope and content of the following claims.

We claim:

1. An apparatus for use in the testing of hollow thermoplastic containers having a variety of shapes and sizes by the application of hot fluid under pressure into the containers comprising, in combination:

a reverse osmosis filter for receiving fluid from an outside source and cleansing such fluid to remove contaminants therefrom;

a heating member for receiving cleansed fluid at a predetermined flow rate and a predetermined pressure from the reverse osmosis filter and heating the fluid to a predetermined temperature and maintaining the fluid at such predetermined temperature at such predetermined flow rate; and an automatic fill member adjustable for the height and volume of the variety of shapes and sizes of hollow thermoplastic container for receiving the heated fluid and injecting the heated fluid at such predetermined temperature and flow rate into the container.

2. The apparatus of claim 1 wherein the reverse osmosis filter includes at least two filter canisters.

3. The apparatus of claim 2, wherein the reverse osmosis filter includes a chlorine removal filter upstream of the filter canisters.

4. The apparatus of claim 2 wherein the reverse osmosis filter includes a large particulate filter upstream of the filter canisters.

5. The apparatus of claim 1 wherein the reverse osmosis filter includes a pressure regulator and a flow rate regulator for setting the fluid pressure and fluid flow rate at predetermined levels before the fluid enters the reverse osmosis filter.

6. The apparatus of claim 1 wherein the reverse osmosis filter includes a recycling port for returning contaminated fluid exiting the filter back to the entrance of the filter.

7. The apparatus of claim 1 wherein the heating member includes at least three heating units, a pressure regulator and a fluid flow regulator wherein the heating member maintains the fluid temperature at a flow rate steady at predetermined levels as the fluid exits the heater.

8. The apparatus of claim 1 further including a normally open valve for receiving the heated fluid from the heating members and directing the fluid to flow from the apparatus to a drain when the apparatus is not in use.

9. The apparatus of claim 8 wherein the open valves closes when the apparatus is in use and directs the heated fluid to a fill nozzle.

10. The apparatus of claim 9 wherein the fill nozzle is automated to engage a container with a specified top load force and fill the container with a specified volume of heated fluid.

11. The apparatus of claim 9 further including an on/off spigot for manual operation as an alternative to the fill nozzle wherein operation of the fill nozzle and operation of the spigot are mutually exclusive.

12. A process for testing hollow thermoplastic containers having a variety of shapes and sizes comprising the steps of:
   a) receiving fluid from a fluid source;
   b) substantially cleansing the fluid of particulate and chemical contaminants;
   c) regulating the flow rate and pressure of the cleansed fluid to preset levels;
   d) heating the cleansed fluid to a preset temperature and maintaining the fluid temperature within preset tolerances of the preset temperature; and
   e) applying the heated fluid to such hollow thermoplastic container.

13. The process of claim 12 wherein the flow rate and temperature of the heated fluid is maintained at a substantially steady state.

14. The process of claim 12 further including the step of removing contaminated fluid from the flow of clean fluid and recycling at least a portion of the contaminated fluid through the cleansing step.

15. The process of claim 12 further including the step of automatically applying the heated fluid to the hollow thermoplastic container at a desired volume and top load to the container.

* * * * *